United States Patent
Ragsdale (10) Patent No.: US 8,222,909 B2
(45) Date of Patent: Jul. 17, 2012

(54) ELECTROPORATION SYSTEM WITH DIAL-IN TIME CONSTANT

(75) Inventor: Charles Ragsdale, Concord, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 438 days.

(21) Appl. No.: 12/535,289

(22) Filed: Aug. 4, 2009

(65) Prior Publication Data
US 2010/0049372 A1 Feb. 25, 2010

Related U.S. Application Data

(60) Provisional application No. 61/091,177, filed on Aug. 22, 2008.

(51) Int. Cl.
  *G01R 27/08* (2006.01)
  *G01R 25/00* (2006.01)
  *C12N 13/00* (2006.01)
(52) U.S. Cl. .................... 324/691; 702/79; 435/173.6
(58) Field of Classification Search ............. 324/691; 702/79
See application file for complete search history.

(56) References Cited

U.S. PATENT DOCUMENTS

| | | | |
|---|---|---|---|
| 5,586,054 A * | 12/1996 | Jensen et al. | 324/533 |
| 6,096,020 A | 8/2000 | Hofmann | |
| 6,798,175 B2 * | 9/2004 | Hanada et al. | 320/166 |
| 7,755,366 B2 * | 7/2010 | Hosoe et al. | 324/601 |
| 2003/0139889 A1 | 7/2003 | Ragsdale et al. | |
| 2006/0025949 A1 * | 2/2006 | McCavit et al. | 702/85 |
| 2008/0076144 A1 | 3/2008 | Ragsdale | |

OTHER PUBLICATIONS

International Search Report and The Written Opinion of the International Searching Authority from International Application No. PCT/US2009/054204 dated Oct. 15, 2009, 10 pages.

* cited by examiner

*Primary Examiner* — Jeff Natalini
(74) *Attorney, Agent, or Firm* — Kilpatrick Townsend & Stockton LLP; David B. Raczkowski (57) ABSTRACT

Methods, systems, and apparatus provide an accurate time constant for electroporation. A model voltage function is created (analog, digital, or combination) to provide a model voltage having the desired time constant. A voltage is applied to the sample. A comparing circuit compares the output voltage, which may be attenuated, to the model voltage and provides an output control signal. This output signal is used to modify a resistance in parallel with the sample, thereby altering the output voltage to approximate the model voltage, which has the desired time constant. In one aspect, the control signal may be used to turn on and off a transistor that is in series with a resistor in order to modify the parallel resistance.

22 Claims, 7 Drawing Sheets

ELECTROPORATION SYSTEM WITH DIAL-IN TIME CONSTANT

CROSS-REFERENCES TO RELATED APPLICATIONS

This application claims the benefit of provisional U.S. Application No. 61/091,177, filed Aug. 22, 2008, entitled "DIAL-IN TIME CONSTANT FOR ELECTROPORATION", the disclosure of which is incorporated herein by reference in its entirety.

The present application also is related to the following commonly-assigned U.S. patent application Ser. No. 11/567,438, entitled "MEASURING SAMPLE RESISTANCE IN ELECTROPORATION," filed on Dec. 6, 2006, by Ragsdale (hereinafter Ragsdale I); and Ser. No. 11/857,679 entitled "RESISTOR PULSE MODULATION," filed on Sep. 19, 2007, by Ragsdale (hereinafter Ragsdale II), which are herein incorporated by reference in their entirety.

BACKGROUND

The present invention relates generally to electroporation systems, and more particularly to providing electroporation systems with accurate, and even user settable, time constants.

It is known that exposure of cells or other biological molecules to intense electric fields for brief periods of time temporarily destabilizes membranes. This effect has been described as a dielectric breakdown due to an induced transmembrane potential, and has been termed "electroporation". Among the procedures that use electroporation are the production of monoclonal antibodies, cell-cell fusion, cell-tissue fusion, insertion of membrane proteins, and genetic transformation.

The cells or tissue are exposed to electric fields by administering one or more direct current pulses. These pulses are administered in an electrical treatment that results in a temporary membrane destabilization with minimal cytotoxicity. The intensity of the electrical treatment is typically expressed in terms of the field strength of the applied electric field. This electric field strength is defined as the voltage applied to the electrodes divided by the distance between the electrodes. Electric field strengths used in electroporation typically range from 250 to 10,000 V/cm For efficient electroporation, it is necessary to control the shape, e.g. time constant of the electrical pulse. For example, electroporation itself occurs within a narrow range of parameters, such as pulse voltage and pulse duration, which is exhibited by a narrow window between electrocution and little or no electroporation. If a pulse with too long a duration or too high a field strength is used, the cells may be lysed (destroyed). If the duration or field strength of a pulse is too low, electroporation efficiency is lost. As an added difficulty, the optimal voltage and time constant varies with the type of cell. The current emphasis on using electroporation to study cells that are sensitive and difficult to transfect (move molecules through membrane) makes the control of electroporation conditions particularly important.

One problem in selecting the electroporation parameters is that the sample itself (cells plus buffer) is a significant factor in the load imposed on an electroporation system, and therefore the time constant. Ragsdale I provides a description of how to measure a resistance of the sample. In theory, a parallel resistance can be set to allow delivery of a pulse with the proper time constant as described in Ragsdale II.

However, the resistance of the sample changes over time, which in turn affects the shape of the electrical pulse that is being applied. For example, the resistance of the sample before the electrical pulse is applied is different than the resistance after X seconds, which is different after further application of the electrical pulse. Thus, it is very difficult to achieve a desired shape of the electrical pulse.

It is therefore desirable to provide methods, systems, and apparatus for achieving a specified time constant, e.g. one that a user can dial-in (i.e. user settable).

BRIEF SUMMARY

Embodiments provide systems and methods for obtaining a desired shape for a time-varying electrical signal that is sent from an electroporation system to a sample. A model voltage function (analog, digital, or combination) is created to provide the desired shape. The electrical signal is then applied to the sample. A comparing circuit compares a voltage (which may be attenuated) of the electrical signal to the model voltage and outputs a control signal. This output signal is used to modify a resistance in parallel with the sample, thereby altering the electrical signal to have the desired shape. In one aspect, the desired shape is one that has a user-settable time constant that defines a rate of decay of the voltage of the electrical signal.

According to one exemplary embodiment, a method of providing an electrical signal to a sample load in an electroporation system is provided. While the electrical signal is provided to the sample load, a first voltage of the electrical signal decreases. This first voltage may be the output voltage received by the sample or a reduced voltage. The first voltage is then compared to a model voltage of the model function that represents a desired decrease of the first voltage of the electrical signal. Based on the comparison, a resistance that is in parallel with the sample load is modified while the electrical signal is being sent to the sample load. The parallel resistance can be modified in such a manner to cause the electrical signal to approximate the model function.

According to another exemplary embodiment, an electroporation system that allows for a time constant or other property for the shape of an electrical signal sent to a sample of the electroporation system to be accurately achieved. A capacitance, which provides an output voltage to the sample load, is selectively coupled with the sample load, e.g., once the capacitance has been charged. A variable resistance device, in parallel with the sample load, is also selectively coupled with the capacitance.

A modeling circuit outputs a model voltage that has a desired shape for the output voltage. A comparing circuit receives the output voltage and the model voltage. Based on a comparison of the two voltages, the comparing circuit outputs a control signal that is sent to an input of the variable resistance device. This control signal modifies a resistance of the variable resistance device. The control signal can be provided in such a manner to cause the electrical signal to approximate the model function.

In one embodiment, an electroporation system comprises a comparing circuit that includes a comparing circuit that includes a voltage reduction circuit that receives the output voltage. The comparing circuit also receives the model voltage. A comparator of the comparing circuit determines a difference between the model voltage and the reduced output voltage and outputs a control signal that is used to control a resistance of the variable resistance device.

A better understanding of the nature and advantages of the present invention may be gained with reference to the following detailed description and the accompanying drawings.

DETAILED DESCRIPTION

It has been a desire for some time to allow a user to dial-in the time constant for electroporation. To achieve the desired time constant for the electrical signal sent during electroporation, embodiments set a capacitance, transmit the electrical signal from the capacitance to the sample, and adjust a resistance in parallel with the sample while the electrical signal is transmitted. The desired shape (e.g. time constant) of the time-varying electrical signal is achieved by modifying the parallel resistance. The proper modification is determined by comparing a voltage of the electrical signal to a model voltage of a model function, which has the desired shape. Accordingly, even if the resistance of the sample changes during exposure to the voltage, the parallel resistance can be modified (e.g. increased or decreased), based on the comparison, to achieve substantially the same shape as the model voltage.

Figure 1:
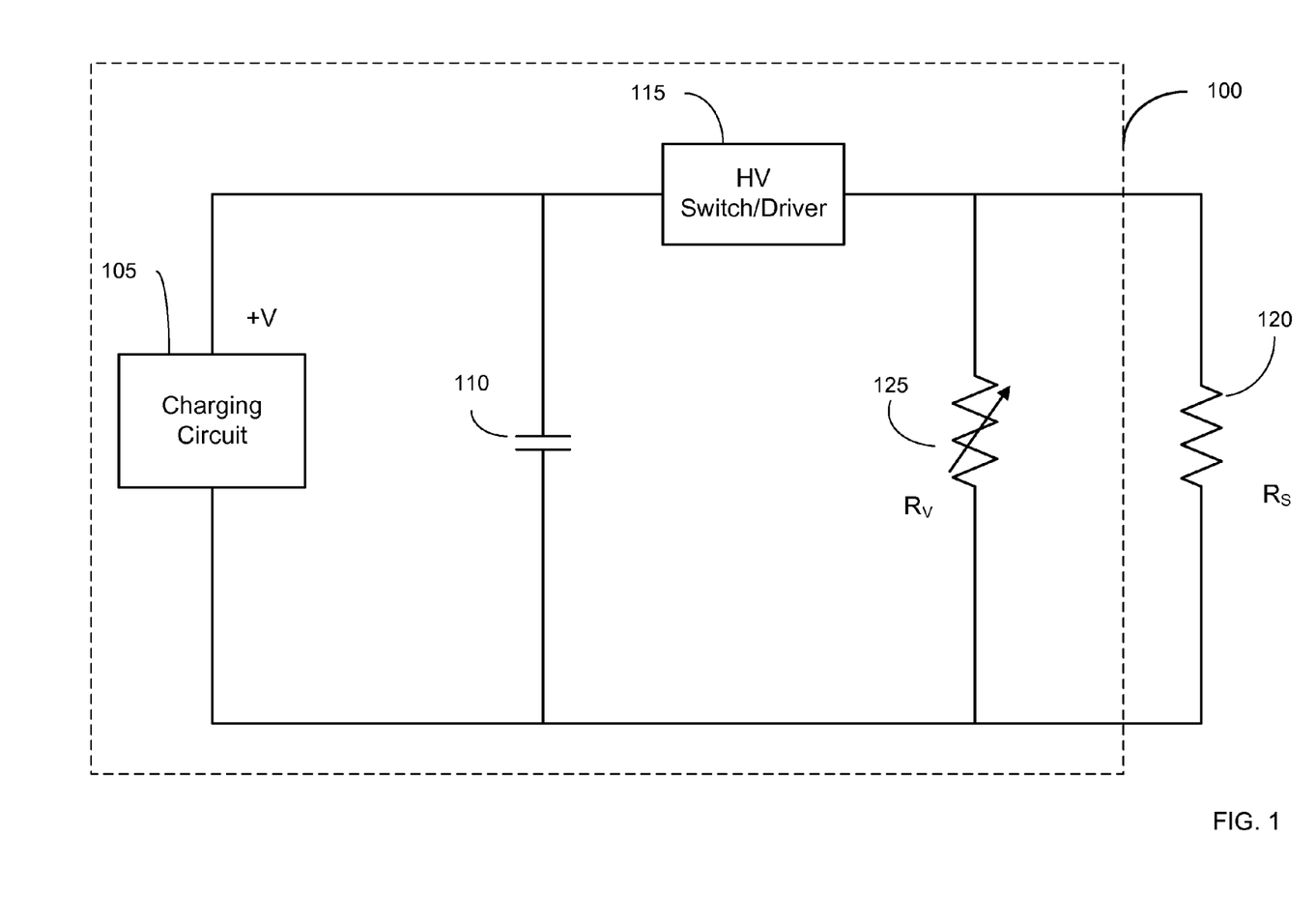
FIG. 1 illustrates an electroporation system 100 according to an embodiment of the present invention.

FIG. 1 illustrates an electroporation system 100 according to an embodiment of the present invention. System 100 transmits an electrical signal to the sample load ($R_S$) 120. The electrical signal causes a time-varying voltage to be felt by sample 120. This voltage can destabilize the membrane of cells in a sample.

When the electroporation system is used for mammalian cells, the voltage is typically 500 V or less. Higher voltages, e.g., up to 3000 V may also be used for other cells. Embodiments of this invention will work with any voltage values. In instances, such as where multiple samples are to be tested or the parameters are to be optimized, sample load $R_S$ 120 may include multiple biological samples, each of which is to receive an electrical signal. In such embodiments, the different samples may reside on a sample plate, such as a microtiter plate, which is arranged in a 2:3 rectangular matrix.

Prior to transmitting the electrical signal, a charging circuit 105 charges at least one capacitor 110. During charging, the switch 115, e.g. a high voltage (HV) switch, is open so that a voltage is not sent to the sample 120 yet. In one embodiment, charging circuit 105 is a power supply or some other constant-power or constant-current source. In another embodiment, HV switch 115 is a driver with programmable parameters, such as number of pulses, pulse duration, and bursts of pulses. Also, capacitor 110 can be set to any number of different capacitance values.

Once charging circuit 105 charges the capacitor 110 to a desired voltage, HV switch 115 is closed. At this point, an electrical signal is transmitted to $R_S$ 120. Examples of the electrical signal include an exponentially decaying pulse, a truncated exponentially decaying pulse, or a square wave signal with droop.

The electrical signal is also sent to a variable resistor $R_V$ 125, which is connected in parallel with $R_S$ 120. The value of the resistance of $R_V$ 125 may be selected or modified to control the electrical signal to have a desired shape. For example, for an exponentially decaying pulse, the resistance of $R_V$ 125 may be determined such that the electrical signal has a desired time constant $\tau = CR$ (which may be substantially equal to a desired pulse duration), where $R = (R_S \times R_V)/(R_S + R_V)$ and C is the capacitance of capacitor 110.

The other variable $R_S$ (resistance of sample 120) can be measured, and then $R_V$ and C may be set to achieve the desired time constant. Where the sample load 125 includes multiple biological samples, the measurement may reflect a combined resistance of all of the samples. Typical methods for measuring $R_S$ require some type of measurement of the sample resistance before the electrical signal (e.g. a pulse) is delivered. Then, the parallel resistance $R_V$ and capacitance C can be set to allow delivery of a pulse with the proper time constant. But, often these methods are not as accurate as needed to accurately control the time constant. For example, inaccuracies in a selected capacitance C can be about 20% and in a selected resistance $R_V$ can be about 10%.

Another problem is that the sample resistance varies with time, the variance is non-linear, and the sample resistance can depend on the voltage being used (e.g., lower with higher voltage). In one aspect, this variability is due, at least partly, to electrolysis of the buffer water. Typically, the electrical pulse would decrease faster than what is desired. To compensate, embodiments change $R_V$ 125 multiple times to maintain the desired shape of the electrical pulse. Different resistances for $R_V$ 125 may be achieved as described in Ragsdale II.

The time constant may be chosen specifically based on the cells or other type of biomolecules in the sample load. As some cells may be sensitive or hard to transfect, a precisely controlled time constant can promote successful electroporation.

In one aspect, the changes made to $R_V$ are based on a model function received from a modeling circuit. The model function may be in analog or digital form. The modeling circuit provides a voltage that is consistent with the desired time constant. The resistance value of $R_V$ is then changed based on a comparison of the actual voltage being applied relative to the model voltage. A description of a system using a modeling circuit follows.

Figure 2:
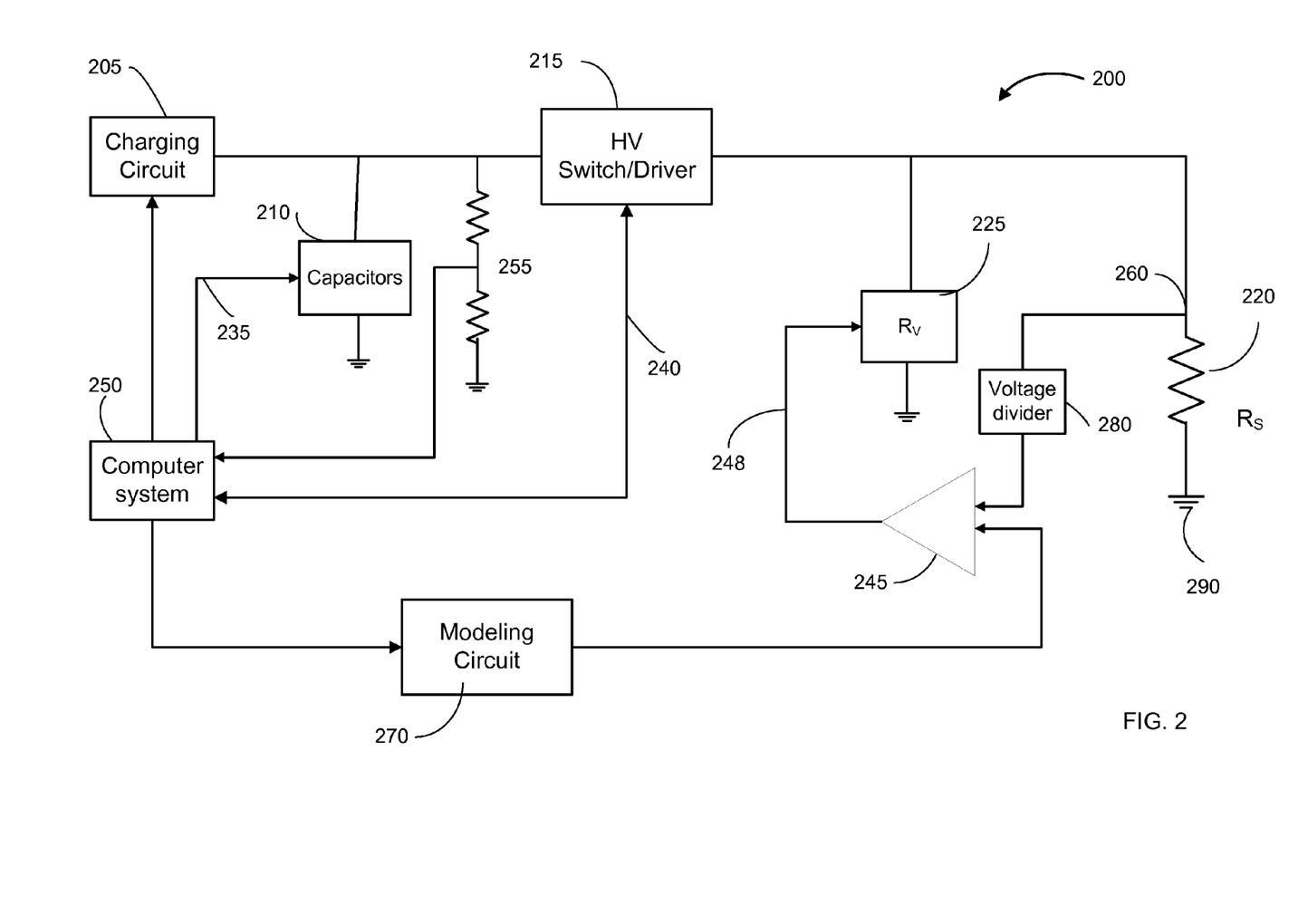
FIG. 2 illustrates an electroporation system 200 having a modeling circuit according to an embodiment of the present invention.

FIG. 2 illustrates an electroporation system 200 having a modeling circuit according to an embodiment of the present invention. System 200 transmits an electrical signal to sample load 220. In one aspect, the transmission of the electrical circuit is controlled (at least partly) by a computer system 250. Lines indicate electrical connections and arrows indicate the flow of information, such as control signals or data.

Computer system 250 may include one or more processors, memory such as RAM, a user interface for input/output, and docking ports for receiving external memory units, such as a CD, thumb drive (e.g. using flash memory), or DVD. The processors may be simple microcontrollers or more complex central processing units.

In one embodiment, computer system 250 receives input parameters for the electrical signal. These input parameters may be entered by the user and/or may be measured (or otherwise detected) by the electroporation system itself. The input parameters may include one or more of (a) waveform (exponential or square wave); (b) specific values or ranges for the voltage (e.g. 10-500V); (c) specific values or ranges for the capacitance (e.g., 25-3,275 mfd); (d) specific values or ranges for the parallel resistance (e.g., 50-1000 ohms); and (e) the resistance of the sample.

Based on the input parameters, computer system 250 selects (e.g. via control line 235) one or more capacitors 210 from a set of available capacitors to achieve a desired capacitance. In one embodiment, electrolytic capacitors are used. In one embodiment, the computer system 250 includes a memory element that contains the capacitance value of each capacitor in the set. The memory element may be flash RAM or any other suitable memory device. Computer system 250 then may select the capacitors that add up to the desired capacitance.

The charging circuit 205 can then receive instructions from computer system 250 to charge capacitance 210 when switch 215, e.g. a high voltage (HV) switch, is open. The instructions may include whether to continue to charge capacitance 210 or at what level to charge it. In one embodiment, the computer system 250 monitors the voltage across the capacitors 210 through a voltage divider 255. When the voltage at capacitance 210 reaches a sufficient value, computer system 250 can signal the HV driver 215 to connect capacitance 210 to the load sample $R_S$ 220 and variable resistor device $R_V$ 225, which is connected in parallel with $R_S$ 220.

At this point, an electrical signal is transmitted to $R_S$ 220 and to $R_V$ 225. In some embodiments, the computer system 250 turns-on and turns-off the HV switch 215 to effect a number of pulses, pulse duration, and bursts of pulses. In one aspect, the electrical signal is an exponentially decaying pulse, a truncated exponentially decaying pulse, or a square wave signal with droop. The square wave signal with droop may be part of an exponentially decaying pulse with a long time constant. After the end of a square wave is reached, the rest of the charge on the capacitance (e.g., the rest of the pulse) may be sent out through another path to ground. In one aspect, a specific percentage of the droop of the square wave is output. Typically, values around 10% are preferred.

An initial value of the resistance of $R_V$ 225 may be set to help obtain the desired shape of the electrical signal. For example, for an exponentially decaying pulse, the resistance of $R_V$ 225 may be automatically determined such that a desired time constant $\tau=CR$ is nominally achieved, wherein $R=(R_S \times R_V)/(R_S+R_V)$ and C is the capacitance of capacitor 210.

The initial value of $R_S$ may be determined by numerous methods, such as those described in Ragsdale I. For example, an AC current with a low voltage may be used prior to transmitting the electrical pulse. The initial value of $R_S$ may also be simply estimated, e.g., based on similarity to other samples with measured resistances.

As the value of $R_S$ changes, the time constant is not achieved to a high degree of accuracy with the initial value of $R_V$ 225. However, modifications to $R_V$ 225 during transmission of the electrical signal can provide the higher accuracy desired.

Modifications to $R_V$ 225 may be determined by monitoring the output voltage of the electrical signal (e.g., an exponential pulse) from the electroporation system 200, e.g., at node 260. Based on differences of the output voltage (e.g., at specific times) from the desired shape, the $R_V$ 225 can be modified to bring the electrical signal closer to the desired shape. In one aspect, the desired shape corresponds to a model voltage that corresponds to the desired voltage of the electrical signal at a particular point in time.

In one embodiment, the differences are determined using a comparing circuit 245. For example, a voltage of the electrical signal is compared to the model voltage using the comparing circuit 245, e.g. comparator. The comparing circuit 245 may be any analog or digital circuitry capable of comparing two values. In the digital regime, analog to digital converters could be employed. In one embodiment, a voltage divider 280 or other voltage reducing circuit is employed so that the comparator may operate at a relatively low voltage.

By way of example, the model voltage may be produced by modeling circuit 270. In one aspect, this model voltage signal has the time constant that is desired. For example, the model can produce an accurate and mathematical relationship between capacitance, resistance, and time, resulting in an exponential waveform with the desired time constant. In one embodiment, the model uses known resistance(s) and capacitance(s) to produce the model voltage, as described in detail later.

Based on the comparison of the output voltage to the model voltage, the comparing circuit 245 produces a control signal 248 that modifies $R_V$ 225. The control signal 128 may be an analog or digital signal. In various embodiments, the control signal 128 can directly set a value for the resistance, change the resistance by an amount proportional to the signal, or change the resistance by a more complicated relationship. Note that any suitable variable resistance device may be used.

In one embodiment, the signal 248 controls a transistor (e.g. in series with a resistor) to turn off and on, and thus operates to control the value of the resistance 225. For example, the transistor may be turned on and off as the high-voltage output waveform goes higher or lower as compared to the modeled waveform.

In another embodiment, the signal 248 could convey an amount of the difference between the voltages, and the resistance could be increased or decreased based on the difference. As an example, to increase the resistance, a width of a pulse width modulated (PWM) signal that is sent to a transistor in series with a resistance may be increased. A further explanation of this and other embodiments can be found in Ragsdale II.

In some embodiments, $R_V$ 225 may be as small as 5 ohms. In such embodiments, multiple resistors may be used in parallel, with the control signal be applied to each transistor in series with the respective resistor.

The computer system 250 may also be able control $R_V$ 225 with a control signal. For example, the computer system 250 may also use a PWM to control one or more transistors.

Figure 3:
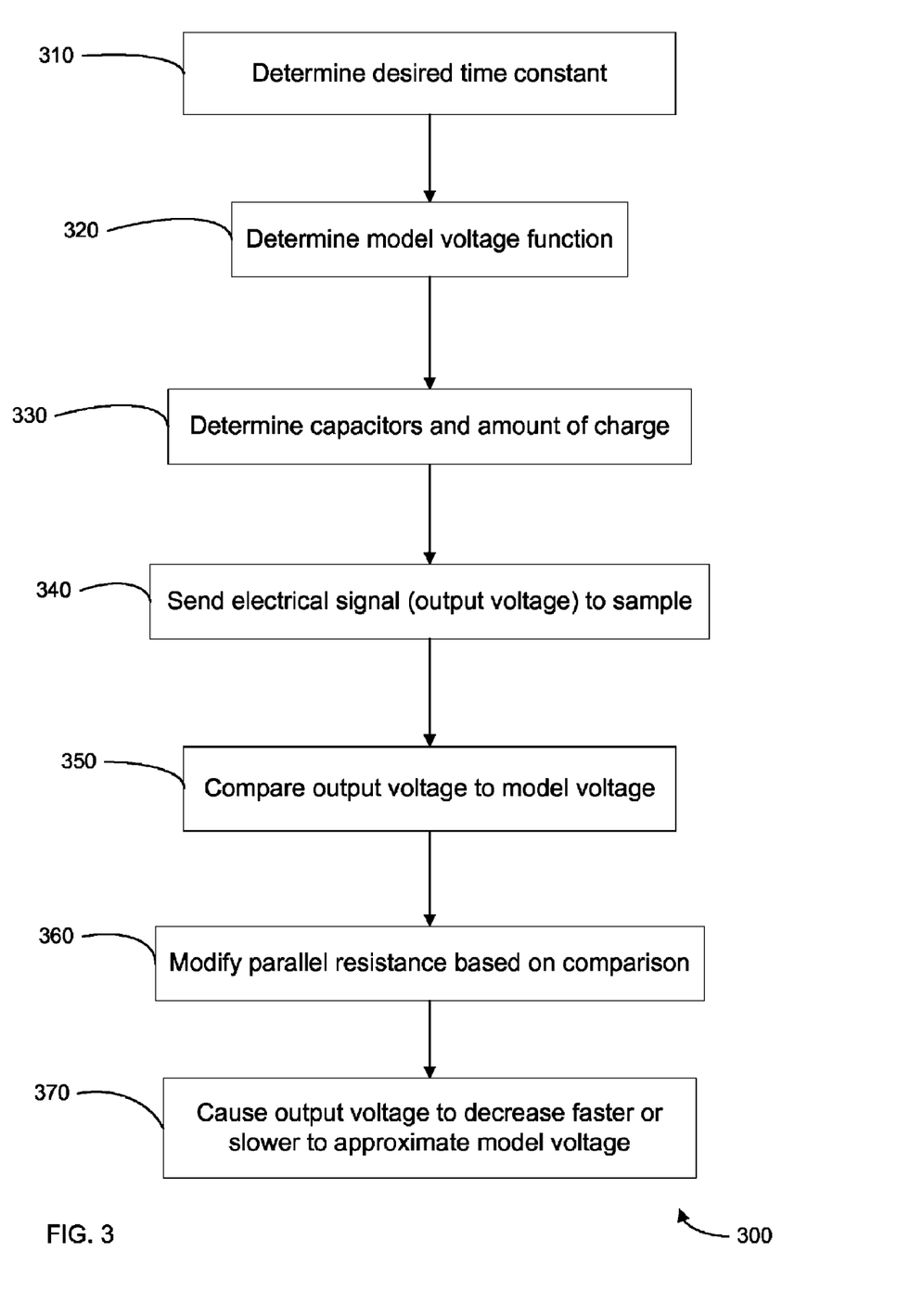
FIG. 3 is a flowchart illustrating a method of providing an electrical signal to a sample load in an electroporation system according to an embodiment of the present invention.

FIG. 3 is a flowchart illustrating a method 300 of providing an electrical signal to a sample load in an electroporation system according to an embodiment of the present invention. Method 300 may be implemented with system 200 or other systems corresponding to embodiments mentioned herein.

In step 310, a desired time constant is determined. In one embodiment, the value for the time constant may be specified by a user of the system 200. The user may just input the desired time constant, letting the system select a nominal C and parallel $R_V$ 235 as appropriate to deliver the desired time constant. In one aspect, the system selects C to keep parallel $R_V$ 235 within a practical range.

The user may select a multitude of other parameters. For example, the user may select a capacitance and simultaneously select the time constant value; the system would then try to provide the selected time constant using a capacitance within a range near the selected capacitance. In one embodiment, a capacitance within approximately 25-30% of the selected capacitance is used; or if the selected capacitance is inconsistent with the selected time constant, a capacitance approximately 25-30% higher than expected would be needed for a guessed value of sample resistance may be used. The user may also select a parallel resistance and simultaneously select a time constant; the system would then determine a capacitance C for capacitors 210 such that the parallel nominal resistance is expected to stay in a range near the selected nominal parallel resistance while delivering the desired time constant.

In another embodiment, the system 200 may determine an appropriate time constant based on the sample. For example, the time constant may be determined by measuring a resistance of the sample. A suitable time constant may then be chosen based just on this resistance, or based on other parameters, which may be input by a user.

In step 320, a model voltage function is determined, e.g., by modeling circuit 270. The model voltage is created to have the desired time constant, or other desired shape. In one embodiment, the model function is simply a series of voltage values as would occur at different points in time. These voltage values may be stored in a memory of the electroporation system.

Figure 6:
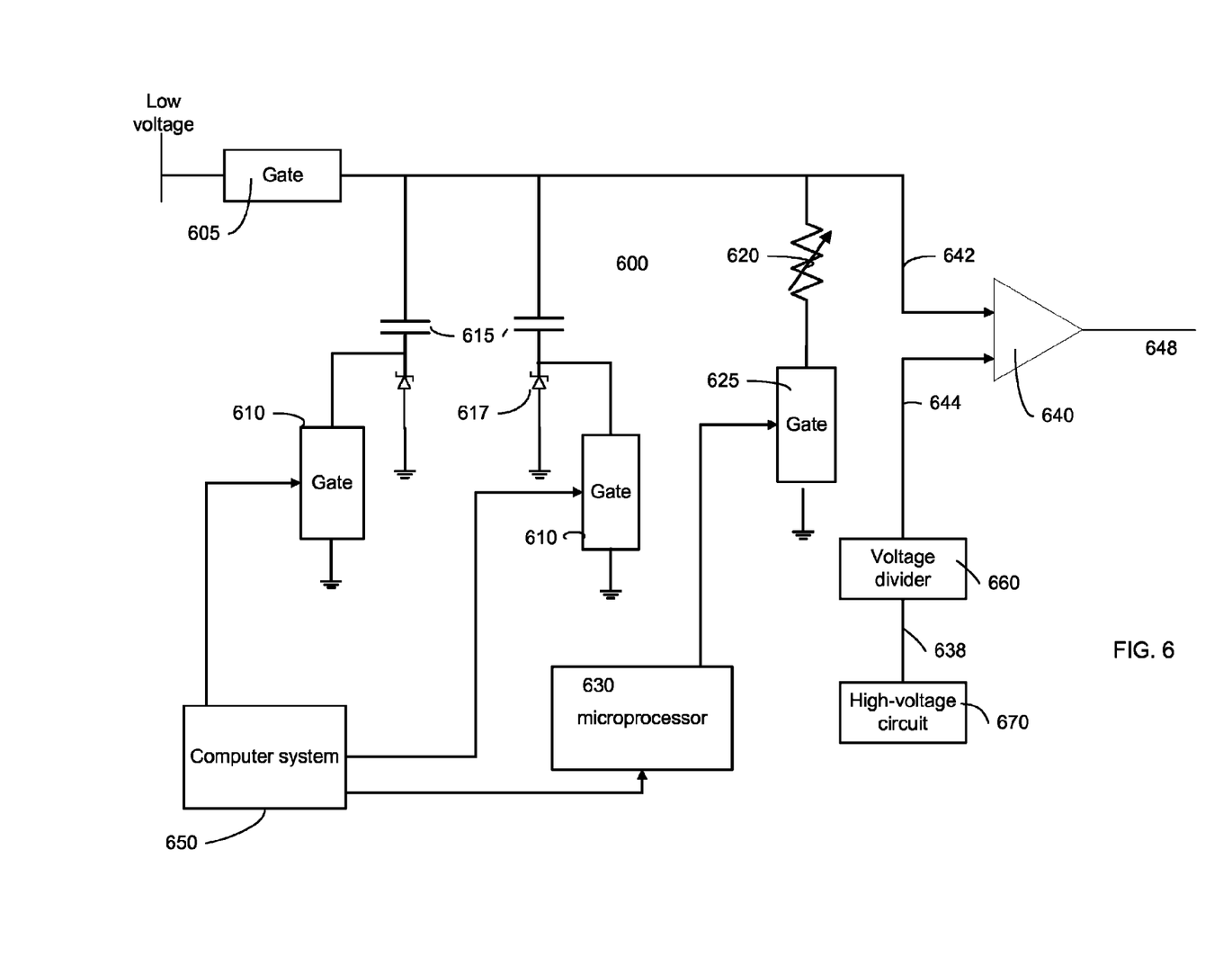
FIG. 6 shows a block diagram of an electroporation system with an analog modeling circuit 600 according to an embodiment of the present invention.

In another embodiment, the model voltage is provided by an RC circuit comprised of a capacitance and resistances that provide the desired time constant. In one aspect, the model R and the C (or the voltage values) to be used are chosen to approximate the actual R (sample resistance and expected parallel resistance) and actual C to be used. However, typically, the R and C values for the model circuit may just have the same (or approximately the same) relative relationship to one another, e.g. the RC of the model circuit is close to the actual RC being used to deliver the electrical signal. For example, typically the model R would be in the range of 1K-2M ohms, which would allow the model C to be in the range of 0.01-2 mfd. The time constant can be chosen typically within 6%, assuming 5% capacitors and 1% resistors in an analog circuit used as modeling circuit 270. FIG. 6 provides a further explanation of this embodiment.

In another embodiment, the model function corresponds to a function that outputs voltage values that decrease at the rate of the desired time constant. For example, the function may be $V_{out}=V_{in}e^{-t/RC}$. An advantage of a digital modeling circuit is that the model voltages can always be reproduced to have exactly the time constant desired.

In step 330, the capacitors and the amount to charge the capacitors is determined. The appropriate capacitance is chosen so the actual time constant can approximate the desired time constant, given the estimated sample resistance. In various embodiments, the capacitance is chosen to be higher than, equal to, or lower than the capacitance of the model voltage.

In one embodiment, the capacitance is chosen to be higher than the desired time constant divided by $R_S$. This selection effectively uses a higher initial time constant so that the parallel resistance $R_V$ can be used to cause a faster decrease in order to achieve the desired time constant. When the parallel resistance $R_V$ is decreased (e.g., by turning on a transistor in series with $R_V$), this decrease effectively lowers the time constant.

In one embodiment, with the parallel resistance not included, the desired time constant would be, e.g., about 25-30% (or up to 50%) shorter than the initial time constant. As just mentioned, once the parallel resistance is turned on, the time constant could then be decreased. And, with the parallel resistance at its smallest value (on all the time in one embodiment), the time constant could, for example, be 50% smaller than the desired time constant.

In step 340, an electrical signal is sent to the sample voltage. Examples of this process are described above. The voltage at some point (node) before the sample is considered the output voltage.

In step 350, the output voltage is compared to the model voltage, e.g. using comparing circuit 245. In one embodiment, part of the comparing includes reducing the output voltage by a prescribed amount prior to a more direct comparison (e.g. a difference) with the model voltage. In one aspect, the prescribed amount is the ratio between the capacitances of the model and high voltage systems.

Both the output voltage and the model voltage are time-varying in that they change over time. Thus, the comparison may be performed multiple times at different instances in time. In one embodiment, the comparison is a continuous calculation, e.g., made by analog circuitry. In one aspect, the comparison may be done very fast. For example, a comparator may oscillate at 100 KHz to 2 MHz.

In another embodiment, the comparison occurs at periodic intervals, e.g., using digital circuitry. The output voltage (or a reduced output voltage) can be converted to a digital value and then compared to a value from a digital circuit (e.g. one that outputs digital values based on a model function).

In step 360, the parallel resistance is modified based on the comparison. In various embodiments, the modification occurs continuously, intermittently, or periodically. The modification may be implemented with the control signal 248 of system 200.

In one embodiment, the parallel resistance is modified when the output voltage crosses the value of the model voltage, i.e. becomes lower, higher, or the same. For example, the control signal 248 can turn-off the parallel resistor 225 (e.g., by turning off a transistor in series with a resistance) when the output waveform is lower than the model voltage. This turning off causes the output voltage to decrease slower than the model voltage decreases, thereby causing the output voltage to align with the model voltage. If the output waveform is higher than that of the model, then the control signal 248 turns-on the parallel resistor, which causes the output voltage to decrease faster than the model voltage decreases.

In another embodiment, the parallel resistance is changed for every comparison operation, or at least for every one where a difference in the voltages changes in a particular direction. For example, the control signal 248 may set or be used to set a particular resistance, i.e. besides an infinite resistance (e.g., disconnecting the parallel resistance device from the circuit). If the difference between the output voltage and the model voltage increases, then the parallel resistance may continue to be increased/decreased as appropriate, e.g., in proportion to the amount of the difference. If the difference between the output voltage and the model voltage decreases, then the parallel resistance may also be changed so as to minimize a difference between the voltages that might occur when the output voltage crosses the model voltage, but with an opposite sign.

In step 370, in response to a modification of the resistance, the output voltage is caused to decrease faster or slower to approximate the model voltage. In other words, the output voltage is brought back in line with the model voltage. Thus, the desired time constant can be achieved. An illustration of one embodiment of modifying the resistance follows.

Figure 4:
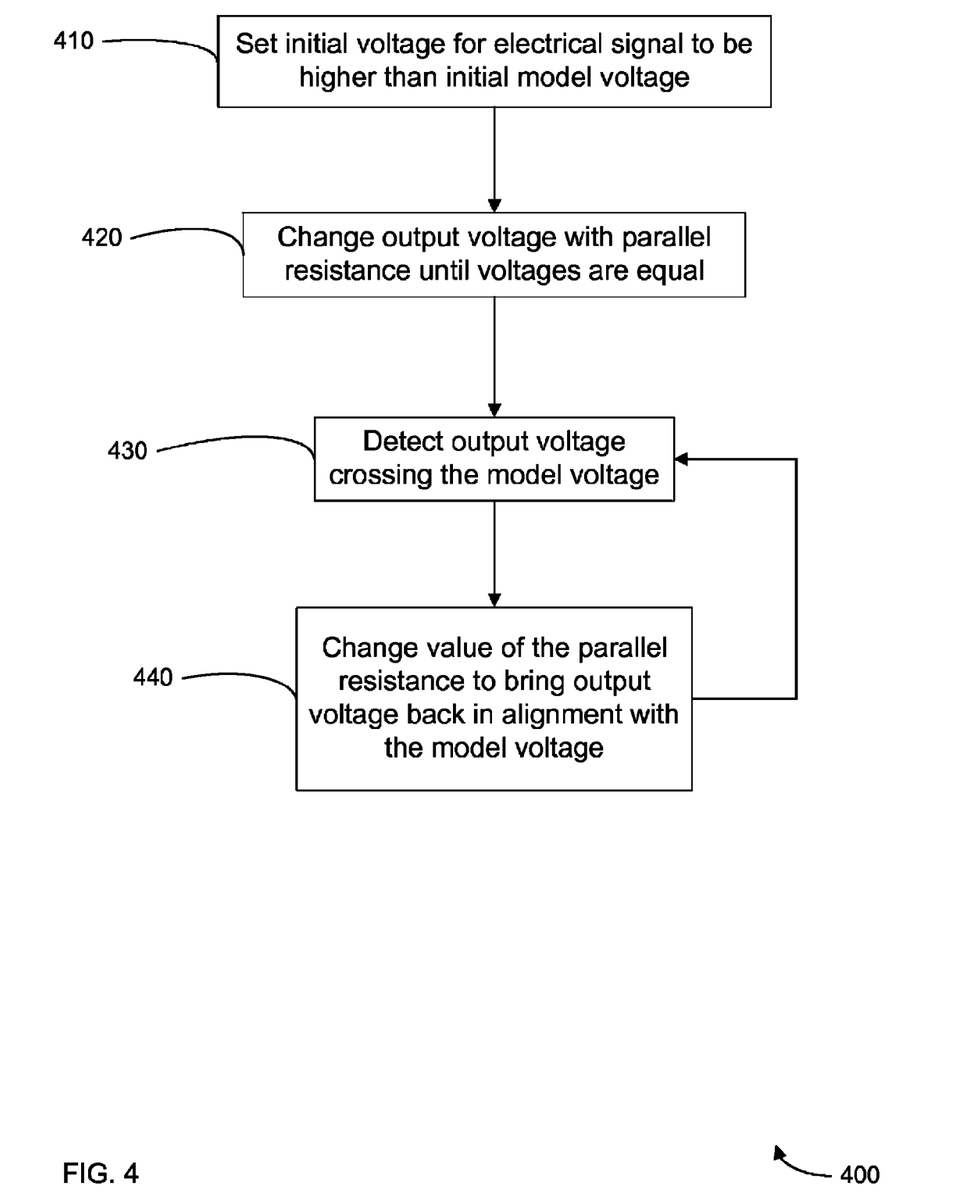
FIG. 4 is a flowchart illustrating a method of altering the parallel resistance to achieve the desired shape of the time-varying electrical signal according to an embodiment of the present invention.
Figures 5A, 5B:
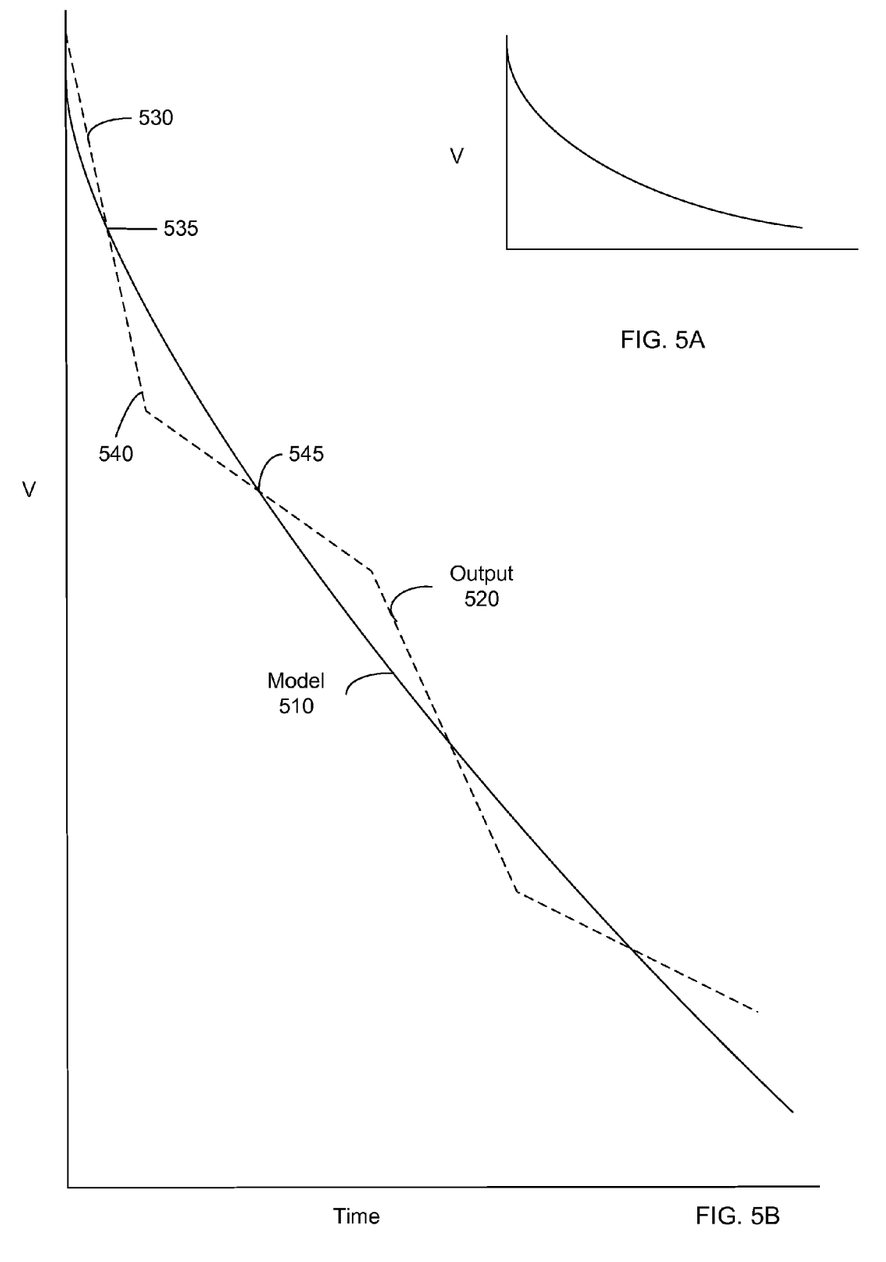
FIG. 5A shows an exponentially decaying waveform according to an embodiment of the present invention.
FIG. 5B shows an example plot of voltage vs. time for the model voltage and the output waveform to illustrate a method according to an embodiment of the present invention.

FIG. 4 is a flowchart illustrating a method 400 for altering the output voltage to approximate a model function by modifying the parallel resistance according to an embodiment of the present invention. As an example, method 400 is presented with reference to FIGS. 5A and 5B to illustrate an embodiment of method 400. FIG. 5A shows an exponentially decaying waveform used as the model function. FIG. 5B shows a magnified view of the exponentially decaying waveform 510 as a plot of voltage vs. time and shows the output voltage 520 according to an embodiment of the present invention. Note that the output voltage 520 may correspond to a reduced output voltage, e.g., as achieved by the voltage divider 280.

In step 410, the initial voltage for the electrical signal is set, e.g., by charging capacitors by a specified amount. As mentioned above, in one embodiment, the high-voltage capacitor 210 is selected to have a capacitance that can produce a longer time constant than the model function when the parallel resistance is not used and a shorter time constant when the parallel resistance is used. In this embodiment, if the initial output voltage (or reduced output voltage as the case may be) is started at the same voltage as the model voltage, the output voltage would: (1) always be higher than the model voltage if the parallel resistance was never part of the circuit; or (2) always be lower than the model voltage if the parallel resistance was always part of the circuit (e.g., as may be controlled by a switch).

In another embodiment, the initial output voltage can be set to start out higher than the model voltage. For example, FIG. 5B shows the output 520 starting out higher than the model voltage 510. In this case, the model function starts out lower than the output electrical signal if the parallel resistance was always part of the circuit, but only for a relatively short period of time.

In yet another embodiment, the initial output voltage can be set to start out lower than the model voltage. In this case, the model function starts out higher than the output electrical signal if the parallel resistance was never part of the circuit, but only for a relatively short period of time.

In step 420, the output voltage is changed with the parallel resistance until the voltages are equal. In the example of FIG. 5B, the output voltage is reduced since the initial output voltage started out higher than the model voltage.

In one embodiment, at the beginning region 530, the output from the comparing circuit 245 provides a signal that activates the parallel resistance 225 because the output 320 is higher than the model 310. For example, a high signal could activate a gate of one or more transistors, effectively creating a parallel drain on the voltage being applied to the sample 220. In one aspect, when the output 520 is higher than the model voltage 510, the parallel resistance 225 is at a minimum value. In other aspects, the value of the parallel resistance 225 is simply small enough to decrease the output 520 faster than the decrease in the model 510.

In step 430, the output voltage is detected crossing the model voltage, e.g., using the comparing circuit 245. For example, the output 520 crosses the model voltage 510 at point 535. This detection may be obtained by identifying a sign change in the difference between the two voltages. The control signal 248 from the comparing circuit 245 may then change based on the change in sign of the difference.

In step 440, the value of the parallel resistance is changed in response to the change in the difference between the two voltages. As shown in FIG. 5B, at point 335, the value of the resistance 225 is increased as now the output voltage 520 is becoming less than the model voltage 510. In one embodiment, the resistance 225 is turned off, effectively providing an extremely high (if not infinite) resistance.

The output 520 may continue to decrease faster than the model 510 due to a lag in the time to compare the two voltages and the time to alter the value of the resistance 225. This lag may be of very short duration. As FIG. 3B is an enlarged view, the amount of lag time may actually be very small. The lines of the output 520 may also be more curved and smoothed, e.g., in part due to the capacitances of the system. Also, at least in one embodiment, the time spacing between transitions will be small in part due to the high speed of a comparator in comparing circuit 245, which will tend to oscillate at high frequency (may be 100 KHz to 2 MHz) in some embodiments.

At some point in region 540, the output 520 begins to increase faster due to the resistance 225 being increased, which drops the amount of charge being drained through the resistance 225. As mentioned above, in one embodiment, the value of the parallel resistance may be changed in a more gradual manner than just off or on. In such an embodiment, the parallel resistance may be decreased at a particular rate until this point in region 540 where the difference between the voltages begins to decrease. At this point, the parallel resistance may be kept steady or begin to increase to prevent a large overshoot.

The method 400 then repeats, a plurality of times, the detection 430 of the output voltage crossing the model voltage and the changing 440 of the parallel resistance. For example, at point 545, the output is larger then the model 520, thus the resistance 225 is turned on, or at least decreased. Thus, the output 520 will again start to decrease faster than the model 510. In this manner, the model voltage is tracked, and the desired time constant is achieved. The time interval over which the monitoring and altering the output voltage may be all of the time period that an electrical signal is sent to the sample or only a portion of the time period.

In one embodiment, although the output voltage 520 is shown to proceed stepwise, the inherent capacitance of the electroporation system can smooth the result. Also, note that the stepwise function is on a very small scale, and thus the output voltage appears to be smooth, and functionally performs as a smooth function.

Figure 7:
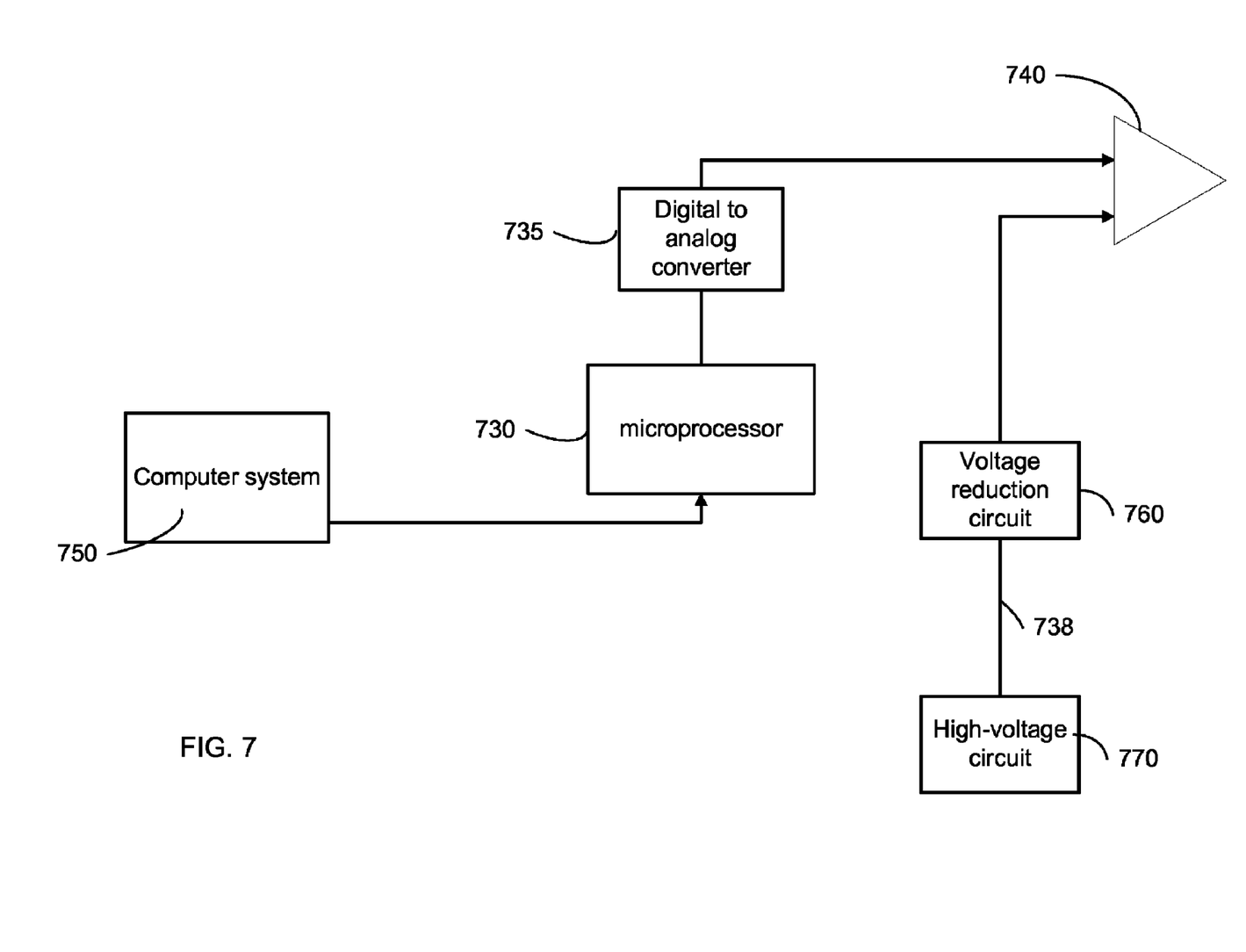
FIG. 7 shows a block diagram of an electroporation system with digital modeling circuit according to an embodiment of the present invention.

As mentioned above, the modeling circuit may implemented in analog, digital, or a combination of both. FIGS. 6 and 7 provide examples of different embodiments.

FIG. 6 shows a block diagram of an electroporation system with an analog modeling circuit 600 according to an embodiment of the present invention. Circuit 600 includes an RC (resistance and capacitance) circuit that outputs a voltage that follows the desired shape (e.g. provides the desired tome constant). In one aspect, this modeling circuit 600 provides a duplicate charging system. However, this system has a total resistance that is controlled.

A series of switches (gates) 610 allow switching-in capacitors 615 in the model circuit. A gate 605 is used to start and stop the charging. Schottky diodes 617 are used to control the discharge. When a gate 610 is on, the corresponding capacitor is selected for charging. The corresponding diode 617 allows proper current flow from a charged capacitor during discharge.

For simplicity, just two capacitor selections are provided by gates 610 and diodes 617. In other embodiments, there are at least 12 capacitor provided such that, for instance, the incremental amount of capacitance available are at least 1% (or even 0.5%) of the total capacitance available.

An electrical signal is sent from the capacitors to a resistance 620 (which may or may not be variable) to release the charge on the capacitors 615, much in the same way that an electrical signal is sent form the capacitors 210 to the sample load 220. The sending of the electrical signal may be started by switching on the gate (switch) 625.

In one embodiment, the value of resistance 620 is chosen to be similar to the total resistance (parallel and sample) of the actual electroporation system. To further control the effective resistance, gate 625 may be controlled using a pulse width modulated (PWM) signal from the computer system 650 or another microprocessor 630. The duty cycle of the PWM signal can be used to set the effective resistance achieved with the resistance 620 and the gate 625. Ragsdale II provides a further explanation of such a procedure. In one aspect, the PWN signal allows adjustment over a 30:1 range, i.e. the duty cycle may vary form being on ⅓₀th of the time (providing 30 times an effective resistance X of one or more resistors) to all of the time (providing the effective resistance X).

In one aspect, the system microprocessor (computer system) 650 passes information to the other microprocessor 630 allowing it to set a duty cycle and thus the parallel resistance of the model circuit. In another aspect, the computer system 650 sets the duty cycle.

In another embodiment, the model circuit 600 works at low-voltage for practical reasons, such as cheaper manufacturing and operating costs. For example, as mentioned above, typically the model R (value of resistance 620 including the effects of the gate 625) would be in the range of 1K-2M ohms, which would allow the model C (capacitors 615) to be in the range of 0.01-2 mfd. A typical voltage range may be 0.02-10.0 V for the model circuit 600. Working in a low-voltage regime also allows for the circuit 600 not to use a switch between the capacitors 615 and the resistance 620, although one may be used.

The voltage 642 is sent to the resistance 620 is also output to a comparator 640 (or some other comparing circuit). The voltage 642 is the model voltage as described above.

Accordingly, in operation, the system microprocessor 650 sets the capacitance (i.e. capacitors 615) in the model circuit and the capacitance of the high-voltage circuit 670. The system microprocessor 650 charges the high-voltage capacitor and delivers the pulse. The comparator 640 compares the model voltage 642 to that of an output voltage 644 received from or derived from the high-voltage circuit 670.

In an embodiment where the model circuit 600 operates at a relatively low voltage, a voltage divider 660, or other circuit for decreasing a voltage, lies between the output 638 from the high-voltage circuit 670 and the comparator 640. The amount of decrease of the voltage corresponds to the difference or ratio of the voltages of the high and low voltage systems.

The output 648 from the comparator 640 can turn-on and turn-off (or otherwise control) the parallel resistance in the high-voltage circuit as necessary to make the output waveform follow the model. Hence, even though the sample resistance behaves non-linearly, the system automatically compensates and makes the output waveform follow the model. In one aspect, the time-constant of the high-voltage circuit needs to be longer than that of the model when the high-voltage parallel resistor R is off and needs to be smaller than that of the model when the high-voltage parallel resistor R is on.

FIG. 7 shows a block diagram of an electroporation system with digital modeling circuit according to an embodiment of the present invention. In this embodiment, the model voltage is provided as discrete digital values corresponding to the model voltage. In one aspect, the digital values may be determined by mathematic functions having an R and/or C as input.

In another aspect, the digital values may be chosen to have any desired shape based on mathematical functions and relationships, or simply based on experimental results or intuition. Thus, each value in the model voltage (i.e. voltage for each time step) may be chosen independent of the other values at different time steps. In this manner, the model voltage is completely flexible and may be made to take on any shape. For example, the a table of voltages may be used.

As shown, a microprocessor 730 provides a digital model voltage value to a digital to analog converter (DAC) 735, which then provides an output to a comparing circuit 740. In one aspect, the digital model voltage value changes at each clock cycle, or after a predetermined number of clock cycles. Although the digital model voltage values do not change continuously, the digital-to-analog converter continuously provides a voltage to the comparing circuit 740

In another embodiment, the microprocessor 730 may provide an analog voltage directly to the comparing circuit 740. In yet another embodiment, the microprocessor 730 provides digital values to the comparing circuit 740.

If digital values are provided to the comparing circuit 740, then an analog-to-digital converter would be used to convert the analog output voltage from the high-voltage circuit 770 (either before or after the voltage decreasing circuit 760) to digital values. The computer system 750 may also provide the model voltage values (digital or analog) and another processor would not be needed. The computer system 750 may also provide the function of the comparing circuit after receiving digital values corresponding to the output voltage from the high-voltage circuit 770.

Typically, the output of the high-voltage circuit 770 is decreased before being compared by the comparing circuit 740 or by the computer system 750, which has a comparing function. In the embodiment shown, a voltage decreasing circuit 760 (such as a voltage divider) receives an output of the high-voltage circuit 770. In another embodiment, the output of the voltage decreasing circuit 760 is sent out the computer system 750 for performing the comparison The specific details of the specific aspects of the present invention may be combined in any suitable manner without departing from the spirit and scope of embodiments of the invention. However, other embodiments of the invention may be directed to specific embodiments relating to each individual aspects, or specific combinations of these individual aspects.

It should be understood that the present invention as described above can be implemented in the form of control logic using hardware and/or using computer software in a modular or integrated manner. Based on the disclosure and teachings provided herein, a person of ordinary skill in the art will know and appreciate other ways and/or methods to implement the present invention using hardware and a combination of hardware and software Any of the software components or functions described in this application, may be implemented as software code to be executed by a processor using any suitable computer language such as, for example, Java, C++ or Perl using, for example, conventional or object-oriented techniques. The software code may be stored as a series of instructions, or commands on a computer readable medium for storage and/or transmission, suitable media include random access memory (RAM), a read only memory (ROM), a magnetic medium such as a hard-drive or a floppy disk, or an optical medium such as a compact disk (CD) or DVD (digital versatile disk), flash memory, and the like. The computer readable medium may be any combination of such storage or transmission devices.

Such programs may also be encoded and transmitted using carrier signals adapted for transmission via wired, optical, and/or wireless networks conforming to a variety of protocols, including the Internet. As such, a computer readable medium according to an embodiment of the present invention may be created using a data signal encoded with such programs. Computer readable media encoded with the program code may be packaged with a compatible device or provided separately from other devices (e.g., via Internet download). Any such computer readable medium may reside on or within a single computer program product (e.g. a hard drive or an entire computer system), and may be present on or within different computer program products within a system or network. A computer system may include a monitor, printer, or other suitable display for providing any of the results mentioned herein to a user.

The above description of exemplary embodiments of the invention has been presented for the purposes of illustration and description. It is not intended to be exhaustive or to limit the invention to the precise form described, and many modifications and variations are possible in light of the teaching above. The embodiments were chosen and described in order to best explain the principles of the invention and its practical applications to thereby enable others skilled in the art to best utilize the invention in various embodiments and with various modifications as are suited to the particular use contemplated.

What is claimed is:

1. A method of providing an electrical signal to a sample load in an electroporation system, wherein a first voltage of the electrical signal decreases while being provided to the sample load, the method comprising:
   determining a time-varying model voltage function for the decrease of the first voltage of the electrical signal as a function of time;
   subsequent to the determining, sending the electrical signal to the sample load, thereby causing an output voltage to be received by the sample load in the electroporation system;
   comparing the first voltage to a model voltage of the time-varying model voltage function at a plurality of times during a time interval in which the time-varying model voltage function is decreasing;
   based on the comparison, modifying a resistance that is in parallel with the sample load while the electrical signal is being sent to the sample load during the time interval.

2. The method of claim 1, wherein the first voltage is the output voltage.

3. The method of claim 1, wherein the first voltage is a reduced voltage that is created by reducing the output voltage by a prescribed amount.

4. The method of claim 1,
   wherein the time interval is at least a portion of the time in which the electrical signal is being sent to the sample load.

5. The method of claim 4, wherein the comparing occurs continually during the time interval.

6. The method of claim 4, wherein the comparing occurs at periodic times during the time interval.

7. The method of claim 6, wherein the model function is represented by digital values at the periodic times, the digital values providing the model voltage.

8. The method of claim 7, further comprising:
   converting the digital values to analog values; and
   providing the analog values to a comparator, wherein comparing the output voltage to the model voltage includes comparing, with the comparator, each of the analog values to the output voltage at respective one of the plurality of times.

9. The method of claim 4, wherein the parallel resistance is modified when the first voltage is different than the model voltage.

10. The method of claim 9, wherein the parallel resistance is decreased when the first voltage is greater than the model voltage, thereby causing the first voltage to decrease faster than the model voltage.

11. The method of claim 9, wherein the parallel resistance is increased when the first voltage is less than the model voltage, thereby causing the first voltage to decrease slower than the model voltage.

12. The method of claim 1, wherein determining the model function is based on a time constant provided by a user of the electroporation system.

13. The method of claim 1, wherein modifying the resistance that is in parallel with the sample load causes the electrical signal to approximate the model function.

14. An electroporation system comprising:
   a capacitance that is selectively coupled with a sample load in the electroporation system and that provides an output voltage to the sample load;
   a variable resistance device that is selectively coupled with the capacitance and that is coupled in parallel with the sample load;
   a modeling circuit that provides a time-varying model voltage;
   a comparing circuit including:
      a first input that receives the output voltage;
      a second input that receives the time-varying model voltage;
      an output coupled with an input of the variable resistance device, wherein the comparing circuit outputs a control signal based on a comparison of the output voltage with the time-varying model voltage at a plurality of times during a time interval, the control signal being received by the input of the variable resistance device and controlling a resistance of the variable resistance device.

15. The electroporation system of claim 14, wherein the voltages received at the inputs of the comparing circuit are represented by digital values.

16. The electroporation system of claim 14, wherein the modeling circuit comprises a processor that determines digital values that are provided as the model voltage to the comparing circuit.

17. The electroporation system of claim 16, wherein the comparing circuit includes an digital-to-analog converter that receives the digital values of the model voltage and that outputs analog values of the model voltage that the comparing circuit uses for the comparison of the output voltage with the model voltage.

18. The electroporation system of claim 16, wherein the comparing circuit includes:
   a voltage divider that reduces the output voltage by a prescribed amount; and
   a comparator that compares the reduced output voltage to the model voltage.

19. The electroporation system of claim 14, wherein the modeling circuit comprises at least one resistance and at least one capacitance and outputs analog values for the model voltage.

20. The electroporation system of claim 14, wherein the variable resistance device includes:
   a resistance; and
   a switch coupled in series with the resistance, wherein the control signal controls whether the switch is open or closed.

21. An electroporation system comprising:
   a capacitance that is selectively coupled with a sample load and that provides an output voltage to the sample load;

a variable resistance device that is selectively coupled with the capacitance and that is coupled in parallel with the sample load;

a modeling circuit that provides a time-varying model voltage;

a comparing circuit including:
- a voltage reduction circuit that receives the output voltage at a first input;
- a second input that receives the time-varying model voltage;
- a comparator that outputs a control signal in response to a difference between the time-varying model voltage and the reduced output voltage at a plurality of times during a time interval, wherein the variable resistance device is coupled with the output of the comparator, and wherein the control signal controls a resistance of the variable resistance device.

22. The electroporation system of claim 21, wherein the controls signal causes the resistance of the variable resistance device to increase when the reduced output voltage is less than the model voltage and causes the resistance of the variable resistance device to decrease when the reduced output voltage is greater than the model voltage.

* * * * *